(12) United States Patent
Barnes

(10) Patent No.: US 6,428,756 B1
(45) Date of Patent: Aug. 6, 2002

(54) COMBINED OZONE GENERATOR AND LIGHT SOURCE

(76) Inventor: Ronald L. Barnes, #74 Revere Way, Huntsville, AL (US) 35801

( * ) Notice: Subject to any disclaimer, the term of this patent is extended or adjusted under 35 U.S.C. 154(b) by 10 days.

(21) Appl. No.: 09/717,903

(22) Filed: Nov. 20, 2000

Related U.S. Application Data

(60) Provisional application No. 60/166,254, filed on Nov. 18, 1999.

(51) Int. Cl.⁷ ................................................ B01J 19/08
(52) U.S. Cl. ............................ 422/186.3; 422/186.07
(58) Field of Search ........................ 422/186.3, 186.07

(56) References Cited

U.S. PATENT DOCUMENTS 4,427,636 A * 1/1984 Obenshain ............. 422/186.07

* cited by examiner

*Primary Examiner*—Kishor Mayekar
(74) *Attorney, Agent, or Firm*—Mark Clodfelter

(57) ABSTRACT

A combination ozone generator for providing ozone and illumination source is disclosed. The ozone generator is of the ultraviolet plasma tube type, with a light guide positioned in or incorporated into the housing of the ozone generator. A phosphor compound is provided on the light guide so that ultraviolet radiation striking the light guide causes the phosphor compound to emit visible light, which is then transmitted away from the ozone generator by the light guide to where it is emitted. Alternate embodiments also disclose the phosphor compounds coating an interior of the housing, and an edge lit panel.

20 Claims, 5 Drawing Sheets

COMBINED OZONE GENERATOR AND LIGHT SOURCE

This application claims priority from provisional application Ser. No. 60/166,254, filed Nov. 18, 1999.

FIELD OF THE INVENTION

This application relates to light sources for swimming pools, spas and the like, and particularly to a combined light source and ozone generator.

BACKGROUND OF THE INVENTION

Most swimming pools and spas need, if not require, illumination. Conventionally, such illumination is provided by incandescent lamps mounted in fixtures provided in sides of the pool or spa. More recently, fiber optics have been utilized in the illumination of swimming pools. Here, one manufacturer provides a relatively large fiber optic bundle consisting of many smaller fibers, along with a lighting unit that is installed remote from the pool. The fiber optic bundle is routed from the lighting unit to a small port below the water level of the pool, where light basically is piped into the pool. One advantage of this system is that when the light bulb fails, it can be easily changed at the location remote from the pool.

In some spas, small, discrete optical fibers are routed from a conventional light source to various locations around the spa where holes are drilled in the side of the spa. The fibers are then simply inserted into the holes so that the end of the fiber is flush with the interior wall of the spa, and the fiber is glued in place, sealing the fiber at the same time.

In these illumination schemes, any sanitization system is independent from the lighting system.

Applicant provides an ozone generator for sanitizing and oxidizing water of the pool or spa, the generator being of the ultraviolet type and which also utilizes the same ultraviolet radiation that generates ozone to provide illumination.

SUMMARY OF THE INVENTION

A combined ozone generator for sterilization of water in a pool or spa is disclosed. Here, an ozone generator utilizing a mercury plasma tube generates ultraviolet light in order to disassociate diatomic oxygen in a flow of air past the tube to form ozone. A variety of light guides and surfaces proximate the plasma tube are coated with phosphor compounds that luminesce in the presence of ultraviolet light. These light guides and surfaces then radiate or pipe the light to where it is radiated.

DETAILED DESCRIPTION OF THE DRAWINGS

In many modern swimming pools and spas, sanitization and clarification of the water is performed in part by ozone generated by an ozone generator. There are several types of ozone generators, one of which having gained wide acceptance is an ozone generator sold by PROZONE INC. of Huntsville, Ala. In this ozone generator, air or oxygen is drawn or forced through a housing containing at least one mercury plasma tube similar to a fluorescent tube, the mercury plasma tube emitting ultraviolet light at wavelengths sufficient to break down diatomic oxygen into molecular oxygen, which then combines with other diatomic oxygen molecules to form ozone. Significantly, the transparent plasma tube is constructed of quartz in order to pass ultraviolet radiation, which is generally blocked by glass, as conventionally found in fluorescent tubes.

The ultraviolet radiation produced by these ozone-generating tubes is relatively intense, more so than in a conventional fluorescent tube. Such intense ultraviolet radiation is capable of producing a substantial light source, similar to that of fluorescent tubes where a phosphor compound that glows when exposed to ultraviolet light coats the inside of the tube. In Applicant's contemplated embodiments, a phosphor compound is coated onto or imbedded into a light guide, which transmits the light to remote locations, which may be in or around a pool or spa. Alternately, light from the tube may be used to illuminate a fluorescent area proximate the tube.

Figure 1:
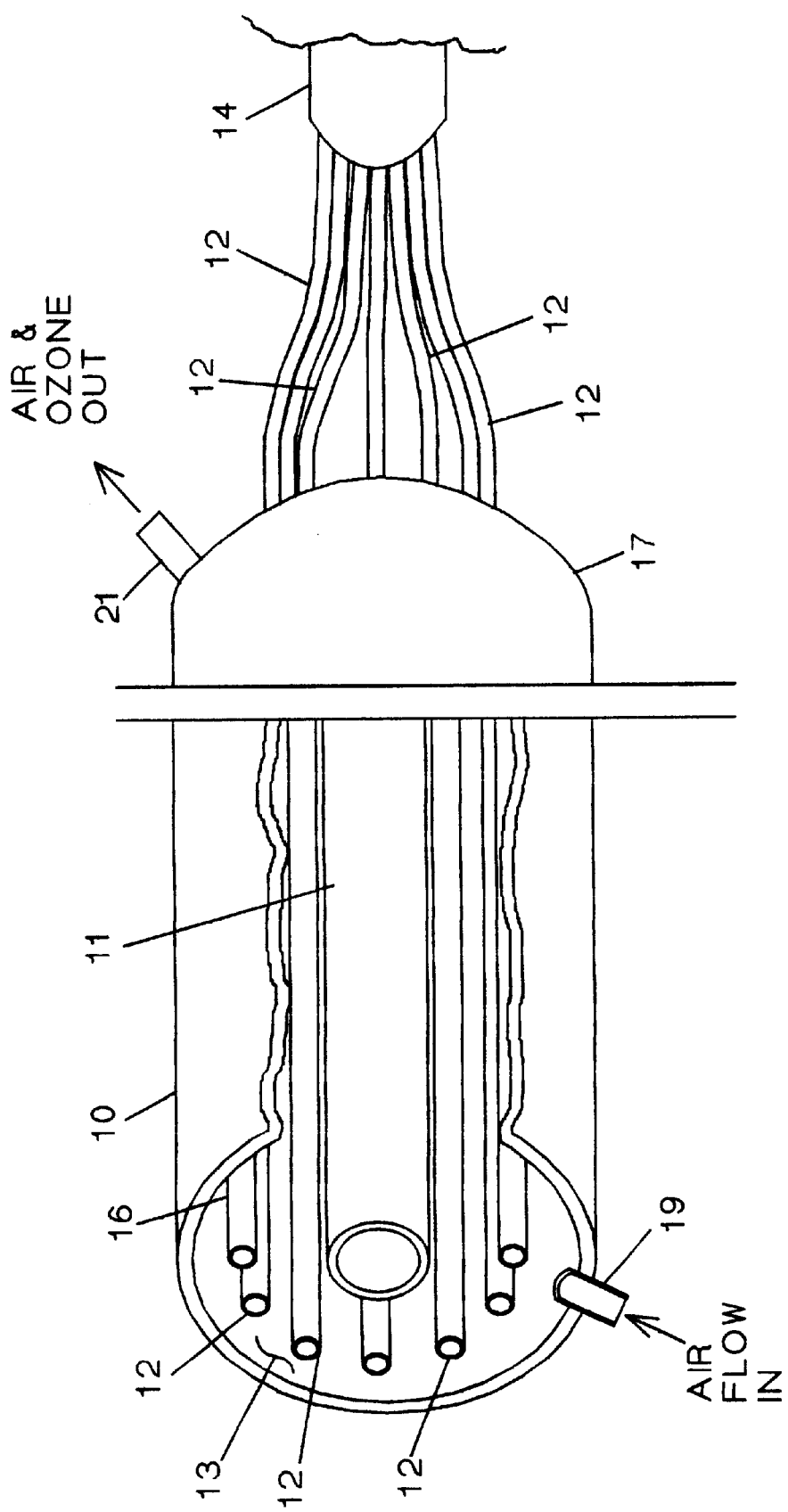
FIG. 1 is a cut-away view showing details of construction of one embodiment of the invention.

Referring to FIG. 1, a cut-away view of one embodiment of an ozone generator housing 10 having one or more ultraviolet tubes 11 and containing one or more light guides 12 is shown. An interior surface 13 of housing 10 would typically be reflective so as to maximize ultraviolet light available to the light guides. In this embodiment, discrete fibers 12 of a fiber optic bundle 14 are provided with a phosphor coating 16 on an exterior side of each fiber. The exterior of each fiber to be coated may be first prepared for receiving light in the visible spectrum by being lightly abraded or etched, after which the phosphor coating may be applied. In this instance, the phosphor coating, in addition to producing visible light, also serves to protect the fiber from degradation due to exposure from ultraviolet light. If desired, a sealant resistant to ultraviolet radiation may be applied over the phosphor coating so as to protect the phosphor from other environmental contamination or degradation. At an end 17 of housing 10, the fibers 12 are consolidated into a bundle 14, which then may be routed to where the light is to be emitted. Alternately, fibers 12 may emerge from both ends of housing 10 (not shown) to form two bundles of fibers. In this instance, the fibers may be constructed having a middle region coated as described with phosphor instead of one end being coated with phosphor. Housing 10 is enclosed generally airtight at both ends, with a conventional inlet port 19 for admitting air into generator 10 and a conventional outlet port 21 for allowing egress of air mixed with ozone for sterilizing water of the pool or spa. Air may be forced into inlet 19 and out outlet 21, as by a small compressor, or drawn by a suction into inlet 19 to outlet 21, as by a venturi device coupled to a flow of water at the pool pump or spa.

Figure 2:
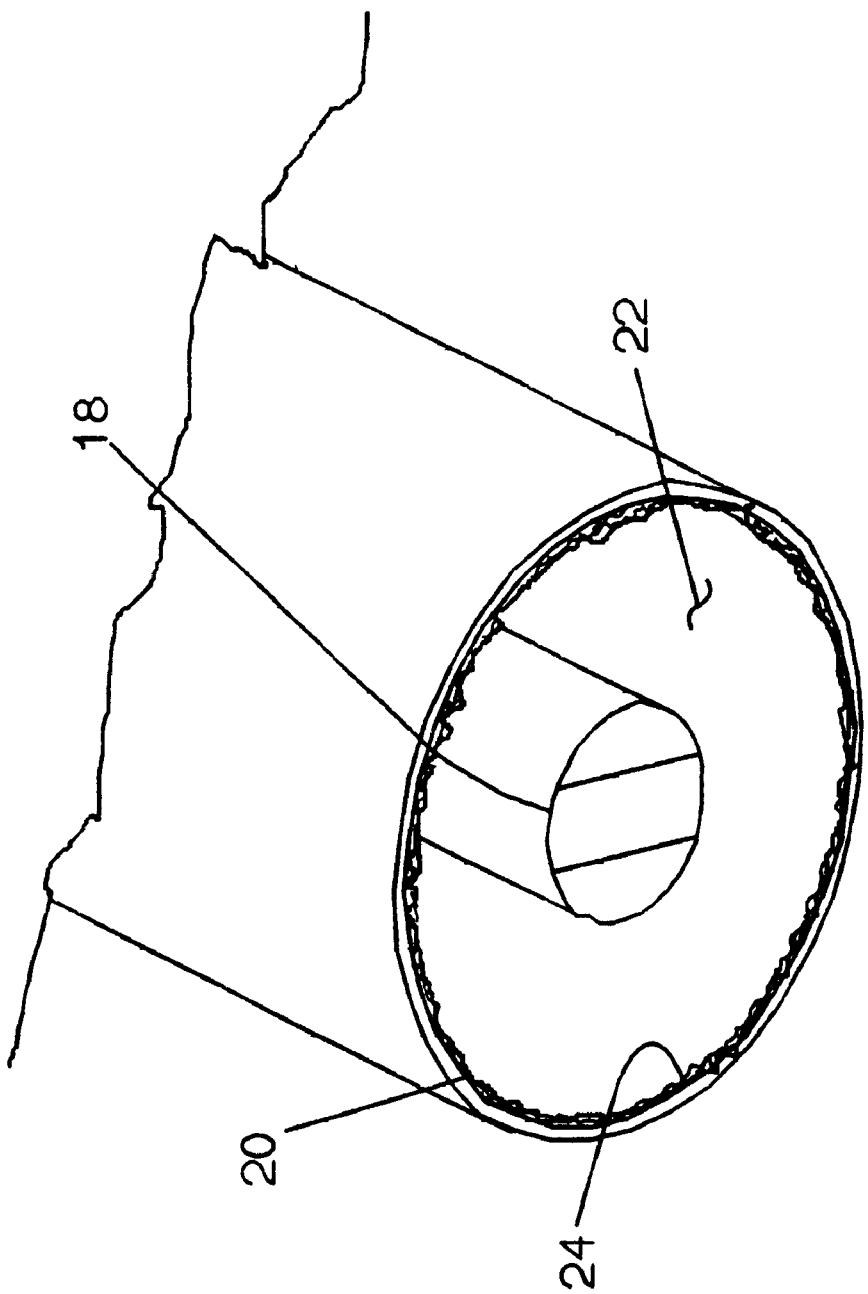
FIG. 2 is a second embodiment showing details of light emitting surfaces and a light guide of the invention.

FIG. 2 shows another embodiment wherein a larger diameter light guide 18 is centrally mounted in its own ultraviolet transmissive housing 20, which may be quartz or other transparent material that passes ultraviolet radiation, with an air gap 22 between light guide 18 and tube 20. A phosphor coating 24 may be applied to an interior or exterior of tube 20, or may be applied to an exterior of or embedded in light guide 18. In this embodiment, tube 20 may be mounted in housing 10 containing at least one ultraviolet tube 11 as shown in FIG. 1, with the housing having an inner reflective surface. Additionally, housing 10 may be configured on the interior as a reflector or collector in order to reflect as much ultraviolet light onto tube 20 as possible. Also in this embodiment, several tubes 20 may be positioned in a housing as shown in FIG. 1.

Figure 3:
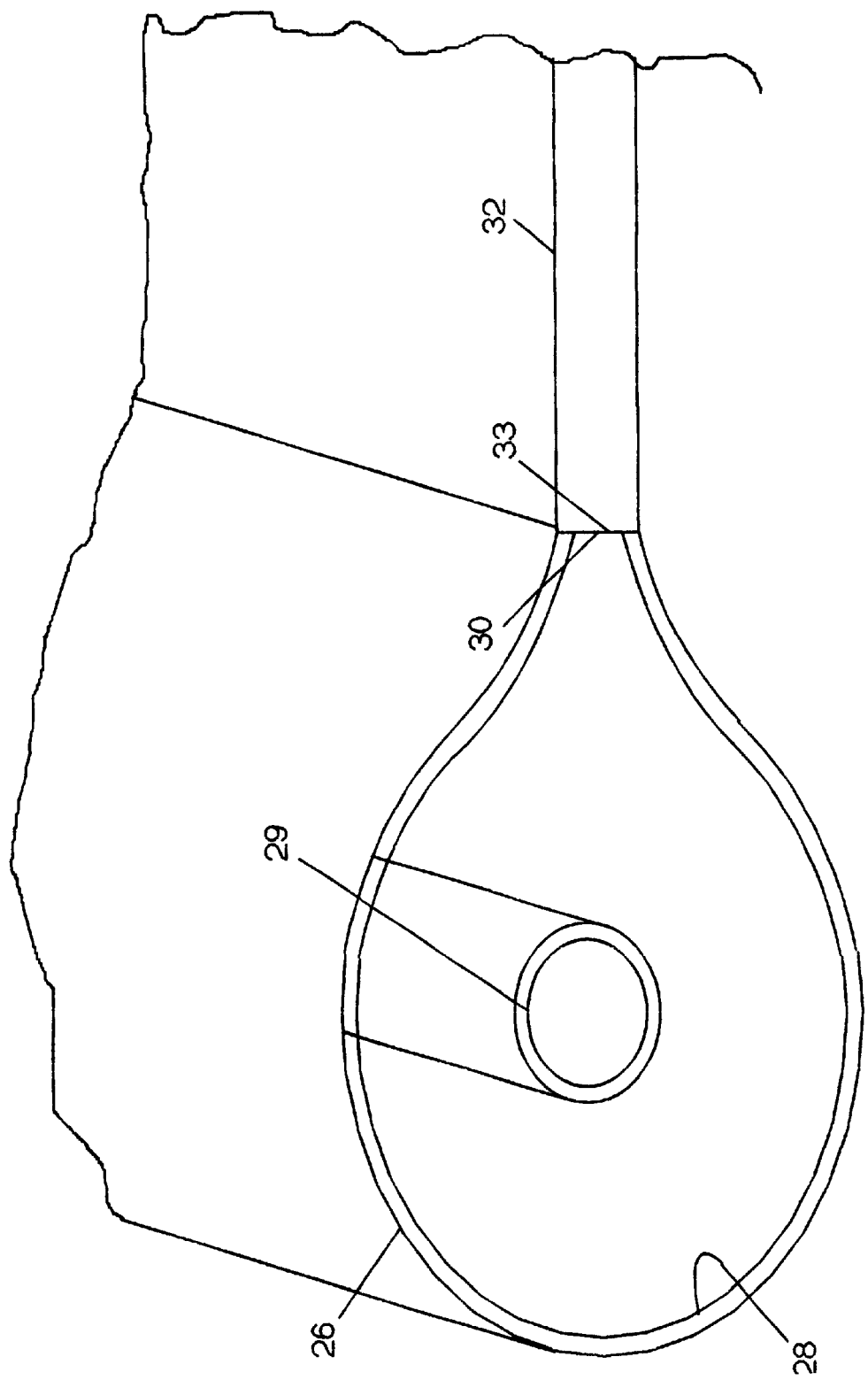
FIG. 3 is a cut-away view showing details of construction of an ozone generator that illuminates an edge lit panel.
Figure 3A:
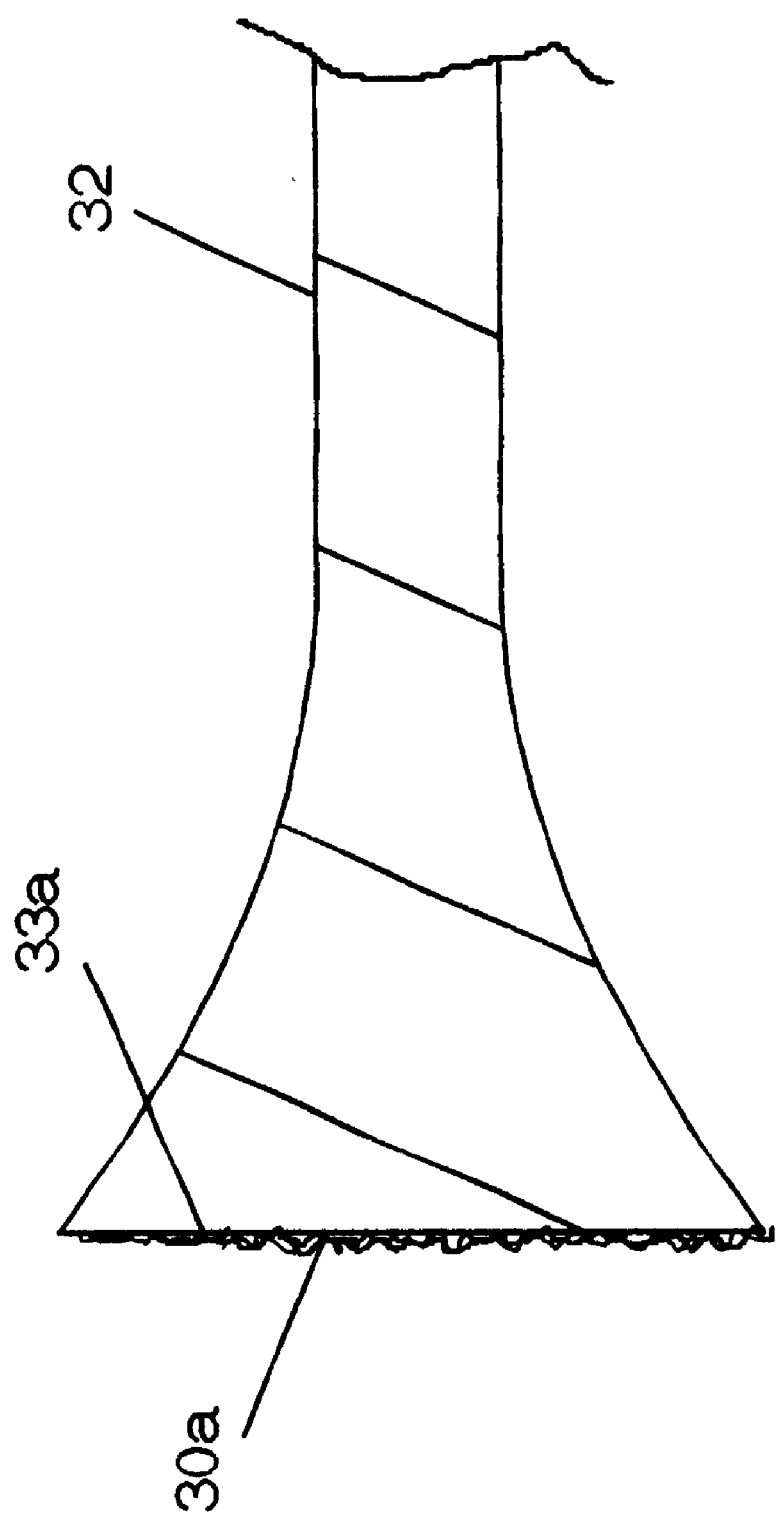
FIG. 3a is a sectional view showing details of construction of the embodiment of FIG. 3

In yet another embodiment as shown in FIG. 3, a housing 26 having an interior reflective surface 28 may be constructed so as to direct ultraviolet light from an ultraviolet tube 29 to an edge 30 of an edge lit panel 32. A layer of phosphor 33 may be layered onto edge 30 or imbedded thereinto a distance of approximately ¼ to ½ inch or so in order to produce visible light at edge 30, which is then transmitted into panel 32. Panel 32 may have advertising media cut or etched into a surface thereof so that the cut or etched areas are illuminated, or light may be emitted linearly from an opposite edge of the panel. One application where the last-described embodiment may be used is in a spa, where such an edge lit panel may be substituted for or mounted in the bottom of the spa, with advertising or other material etched or cut in a face of the panel, the cut or etched media facing upwards. As such, users or viewers of the spa would be exposed to the illuminated advertising media, with the illumination also serving the additional purpose of providing illumination for the spa. Such a panel may also be built into the bottom of a spa, with designs cut in the portion of the panel that is seen from above. Alternately, instead of designs, a pattern may be cut into the panel so as to intercept and direct upward as much light as possible for illumination purposes. Of course, an edge of the panel at the side of the spa would be coated with phosphors as described and adapted to be fitted into close proximity with an ultraviolet tube of the ozone generator, which would also be constructed to receive the edge of the panel. In addition, the edge of the panel proximate the ultraviolet tube may be enlarged, as shown in FIG. 3a, to several times the thickness of the panel to provide an edge of increased area 30a onto which phosphors 33a may be coated, with this enlarged edge configured to transmit light from the increased surface area 30a of the enlarged edge into the panel. This would increase luminosity of light radiated from the bottom of the spa.

Figure 4:
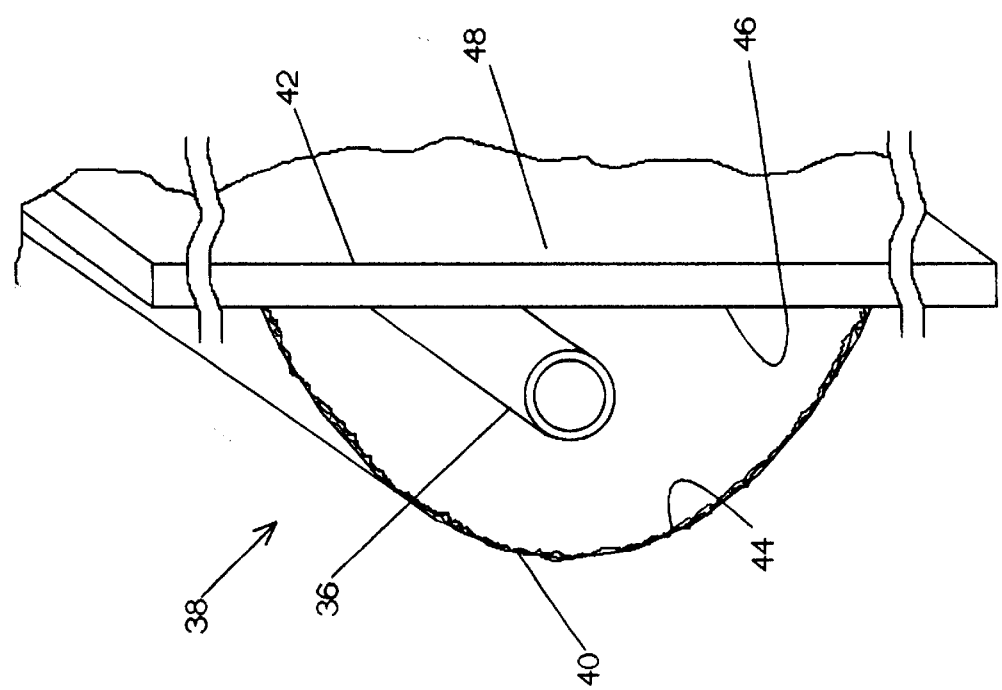
FIG. 4 is a cut away view showing an ozone generator having one side thereof configured as a flat, illuminated panel.

In a variation of this embodiment, as shown in FIG. 4, an ultraviolet tube 36 is shown mounted in an ozone generator housing 38 configured having one side 40 curved along an axis of tube 36, which curve may be a parabola, with the other side 42 being a transparent or translucent plate. The housing for this embodiment may be a tube, such as PVC, bisected lengthwise to form the curved portion of the housing, which may then be bonded or otherwise attached to side 42. In this instance, phosphor may be applied to an inner surface 44 of side 40 so that visible light is emitted through side plate 42. In another embodiment, an inner side 46 of side plate 42 may be coated with phosphor and inner side 44 made reflective so that ultraviolet light from tube 36 is reflected to the phosphors coating an inside surface 46 of side plate 42 to generate visible light. Of course, light from tube 36 that impinges directly on surface 46 also generates visible light. Also, both surfaces 44 and 46 may be coated with phosphors. This embodiment has particular application as a sign, with advertising or other media cut or etched into a front or rear 48 of side plate 42. In yet a third embodiment, side 48 may have the phosphor compounds incorporated thereinto. Additionally, since side 40 is curved, light is either emitted or reflected into side plate 42 at angles to enable significant light emission from an edge of plate 42 and to illuminate a side plate 42 that is much larger than an area occupied by housing 38.

In yet another embodiment, the entire housing itself may be tubular, and constructed of a transparent material with the entire inner surface coated with the phosphor compound so that the entire housing emits light and becomes a light source. Alternately, the compound the housing is constructed of may have the phosphors incorporated therein so that the entire housing glows during operation In any of the above described embodiments, and as stated, the housing containing the ultraviolet radiation tubes is configured as a housing for an ozone generator. As such, the housing may be generally airtight, with an inlet, or openings that serve as inlets to allow air to enter the housing, and an outlet for exhausting or removing air containing ozone. Air may be forced into the inlet, as by a compressor, or drawn into the inlets from the outlet by a suction applied at the outlet, as by a venturi device. In any case, a flow of air containing oxygen is provided through the housing and past the ultraviolet tubes, which in turn convert some of the diatomic oxygen to ozone. The ozone is then mixed with water from the pool or spa to effect sterilization thereof, as is well known in the art.

Having thus described my invention and the manner of its use, it should be apparent to one skilled in the art that incidental modifications may be made thereto that fairly fall within the scope of the following appended claims, wherein I claim:

1. A combined ozone generator and light source comprising:
   a generally airtight housing having at least one air inlet and an air outlet for allowing air to flow through said housing,
   at least one ultraviolet tube positioned in said housing, said ultraviolet tube configured to emit ultraviolet radiation,
   at least one light guide having a first portion thereof positioned generally proximate said ultraviolet tube and a second portion extending away from said first portion, and
   at least one phosphor compound in said housing and configured to emit visible light in a presence of said ultraviolet radiation, said visible light entering said light guide and radiated away from said housing.

2. A combined ozone generator and light source as set forth in claim 1 wherein an interior of said housing is reflective to reflect light to said light guide.

3. A combined ozone generator and light source as set forth in claim 1 wherein said light guide includes a plurality of fiber optic conductors positioned in said housing and extending therefrom to form at least one fiber optic bundle, with said phosphor compound coating an exterior portion of each said fiber optic light conductor within said housing.

4. A combined ozone generator and light source as set forth in claim 1 wherein at least one said light guide is enclosed in a transparent tube within said housing, said transparent tube having a coating of said phosphor compound associated therewith so that said visible light is received by said light guide and transmitted away from said housing.

5. A combined ozone generator and light source as set forth in claim 4 wherein at least one of an inner surface or outer surface of said transparent tube is coated with said phosphor compound.

6. A combined ozone generator and light source as set forth in claim 1 wherein said light guide is configured generally as a plate of light conductive material, with said phosphor compound associated with an edge of said plate configured to be mounted proximate said ultraviolet tube and within said ozone generator, said plate configured to function as an edge lit panel.

7. A combined ozone generator and light source as set forth in claim 6 wherein said housing is configured to reflect said ultraviolet radiation onto said edge.

8. A combined ozone generator and light source as set forth in claim 6 wherein said phosphor compound is coated onto said edge.

9. A combined ozone generator and light source as set forth in claim 6 wherein said phosphor compound is incorporated in said edge.

10. A combined ozone generator and light source as set forth in claim 6 wherein said edge is enlarged to provide a greater surface area with which to collect said ultraviolet radiation, thereby providing increased luminescence to said edge.

11. A combined ozone generator as set forth in claim 1 wherein said light guide is configured as a plate incorporated into said housing such that a side of said plate receives said ultraviolet radiation.

12. A combined ozone generator and light source as set forth in claim 11 wherein an interior side of said housing is configured to reflect said ultraviolet radiation toward said side.

13. A combined ozone generator and light source as set forth in claim 11 wherein an interior surface of said housing is coated with said phosphor compound.

14. A combined ozone generator and light source as set forth in claim 11 wherein a surface of said plate exposed to said ultraviolet radiation is coated with said phosphor compound.

15. A combined ozone generator and light source as set forth in claim 11 wherein said phosphor compounds are incorporated in said plate.

16. A combined ozone generator and light source comprising:

a generally airtight, elongated housing containing an ultraviolet tube therein and having an air inlet and an air outlet, said housing configured to pass a flow air between said air inlet and said air outlet, at least one light guide in said housing, said light guide extending generally the length of said housing and generally parallel with said ultraviolet tube, and further extending from said housing so as to conduct light away from or to a point remote from said housing, and at least one phosphor compound within said housing to emit visible light in the presence of ultraviolet radiation from said ultraviolet tube, said visible light transmissable to said light guide for transmission away from said housing.

17. A combined ozone generator and light source as set forth in claim 16 wherein said light guide comprises a plurality of fiber optic light conductors positioned around said ultraviolet tube, with a portion of each said fiber optic conductor within said housing coated with said phosphor compound.

18. A combined ozone generator as set forth in claim 16 wherein said light guide is constructed as a portion of a side of said housing.

19. A combined ozone generator as set forth in claim 18 wherein said light guide is configured as a plate, with an edge of said plate mounted generally parallel with said ultraviolet tube.

20. A combined ozone generator as set forth in claim 18 wherein said light guide is configured as a plate, with a side of said plate incorporated in said housing so that said visible light is transmitted through said plate for generally the length of said housing.

* * * * *